United States Patent
Eisinger et al.

(10) Patent No.: US 8,126,550 B2
(45) Date of Patent: Feb. 28, 2012

(54) METHODS AND DEVICES INVOLVING AUTOMATIC ATRIAL BLANKING

(75) Inventors: George E. Eisinger, Scottsdale, AZ (US); Jeffery D. Snell, Chatsworth, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 889 days.

(21) Appl. No.: 12/177,405

(22) Filed: Jul. 22, 2008

(65) Prior Publication Data

US 2010/0023083 A1   Jan. 28, 2010

(51) Int. Cl.
*A61N 1/18* (2006.01)

(52) U.S. Cl. ............................ 607/9; 607/17

(58) Field of Classification Search ............... 607/9, 14, 607/17
See application file for complete search history.

(56) References Cited

U.S. PATENT DOCUMENTS

| | | | |
|---|---|---|---|
| 4,712,555 A | | 12/1987 | Thornander et al. |
| 4,825,870 A | * | 5/1989 | Mann et al. ............... 607/9 |
| 4,920,965 A | | 5/1990 | Funke et al. |
| 4,940,052 A | | 7/1990 | Mann et al. |
| 4,944,298 A | | 7/1990 | Sholder |
| 5,269,299 A | | 12/1993 | Duncan |
| 5,400,796 A | | 3/1995 | Wecke |
| 5,441,523 A | * | 8/1995 | Nappholz ............... 607/14 |
| 5,466,254 A | | 11/1995 | Helland |
| 5,476,483 A | | 12/1995 | Bornzin et al. |
| 5,584,867 A | | 12/1996 | Limousin et al. |
| 5,591,214 A | | 1/1997 | Lu |
| 5,653,738 A | | 8/1997 | Sholder |
| 5,778,881 A | | 7/1998 | Sun et al. |
| 6,169,918 B1 | * | 1/2001 | Haefner et al. ............... 600/509 |
| 6,459,928 B2 | | 10/2002 | Mika et al. |
| 6,477,416 B1 | | 11/2002 | Florio et al. |
| 6,553,258 B2 | | 4/2003 | Stahmann et al. |
| 6,564,097 B1 | | 5/2003 | Williams et al. |
| 6,625,490 B1 | | 9/2003 | McClure et al. |
| 6,650,931 B1 | | 11/2003 | McClure et al. |
| 6,912,418 B1 | * | 6/2005 | Florio ............... 607/9 |
| 6,920,355 B2 | * | 7/2005 | Baker et al. ............... 607/9 |
| 6,934,585 B1 | | 8/2005 | Schloss et al. |
| 2003/0097157 A1 | | 5/2003 | Wohlgemuth et al. |

OTHER PUBLICATIONS

Barold, S. Serge et al., "Complex Manifestations of an Automatic Mode Switching Algorithm," PACE. 2007;30:112-114.
Kawanishi, David et al., "Closer investigation of oversensing: sense amplifier signal analysis," Europace 2001. 2 (Supp B):B146—Abstract 454.
Queiroga, Andre et al., "Overdrive pacing for atrial fibrillation—complications and ways to overcome them," Europace 2001;2(Supp B):B203—Abstract 648.
NonFinal Office Action, mailed Oct. 10, 2006: Related U.S. Appl. No. 10/979,833.
Final Office Action, mailed Jul. 13, 2007: Related U.S. Appl. No. 10/979,833.

* cited by examiner

*Primary Examiner* — Carl H Layno
*Assistant Examiner* — Luther Behringer

(57) ABSTRACT

During a period of time comprising a plurality of cardiac cycles, a time relationship between ventricular events and atrial detections is established. Based on the relationship, a post-ventricular atrial refractory period is defined. The period includes an absolute atrial refractory period and a segmented relative atrial refractory period, wherein the segmented relative atrial refractory period includes at least one blanking window during which atrial detections of ventricular events have or are likely to occur.

14 Claims, 11 Drawing Sheets

| 1 | 2 | 3 | 4 | 5 | 6 | 7 | 8 | 9 | 10 | 11 | 12 |
|---|---|---|---|---|---|---|---|---|---|---|---|
| V/R | | | | | | | | | | | |
| $T_{v1}$ | | | | | | | | | | | |

DATA ACQUISITION BUFFER – START OF CYCLE

*FIG. 7A*

| 1 | 2 | 3 | 4 | 5 | 6 | 7 | 8 | 9 | 10 | 11 | 12 |
|---|---|---|---|---|---|---|---|---|---|---|---|
| V/R | P1 | P2 | P3 | | | | | | | | |
| $T_{v1}$ | $T_{v1}+T_{p1}$ | $T_{v1}+T_{p2}$ | $T_{v1}+T_{p3}$ | | | | | | | | |

DATA ACQUISITION BUFFER – P-DETECTION SET RECORDED

*FIG. 7B*

| 1 | 2 | 3 | 4 | 5 | 6 | 7 | 8 | 9 | 10 | 11 | 12 |
|---|---|---|---|---|---|---|---|---|---|---|---|
| V/R | P1 | P2 | P3 | V/R | | | | | | | |
| $T_{v1}$ | $T_{v1}+T_{p1}$ | $T_{v1}+T_{p2}$ | $T_{v1}+T_{p3}$ | $T_{v2}$ | | | | | | | |

DATA ACQUISITION BUFFER – END OF CYCLE

*FIG. 7C*

| 1 | 2 | 3 | 4 | 5 | 6 | 7 | 8 | 9 | 10 | 11 | 12 |
|---|---|---|---|---|---|---|---|---|---|---|---|
| V/R | | | | | | | | | | | |
| $T_{v2}$ | | | | | | | | | | | |

DATA ACQUISITION BUFFER – START OF NEXT CYCLE

*FIG. 7D*

METHODS AND DEVICES INVOLVING AUTOMATIC ATRIAL BLANKING

CROSS REFERENCE TO RELATED APPLICATIONS

This application is related to copending U.S. patent application Ser. No. 12/116,450, filed May 7, 2008, titled "System and Method for Detecting Hidden Atrial Events for Use with Automatic Mode Switching Within an Implantable Medical Device"; and to copending U.S. patent application Ser. No. 12/118,423, filed May 9, 2008, titled "Determining Atrial Time Periods in Conjunction with Real-Time Testing."

FIELD OF THE INVENTION

The invention relates generally to implantable cardiac devices, and more particular to such devices and related methods that implement a segmented post-ventricular relative atrial refractory period including one or more blanking windows, wherein far-field signals have or are likely to occur.

BACKGROUND OF THE INVENTION

Implantable cardiac devices ("ICDs") are well known in the art, and may operate to treat a variety of heart conditions. Generally ICDs are designed to monitor and stimulate the heart of a patient who suffers from a cardiac arrhythmia. Using leads connected to a patient's heart, these devices typically stimulate the cardiac muscles by delivering electrical pulses in response to measured cardiac events that are indicative of a cardiac arrhythmia. Properly administered therapeutic electrical pulses often successfully reestablish or maintain the heart's regular rhythm.

ICDs may treat a wide range of cardiac arrhythmias by using a series of adjustable parameters to alter the energy, shape, location, and frequency of the therapeutic pulses. The adjustable parameters are usually defined in a computer program stored in a memory of the ICD. The program, which is responsible for the operation of the ICD, may be defined or altered telemetrically by a medical practitioner using an external implantable device programmer.

Programmable ICDs are generally of two types: single-chamber ICDs, and dual-chamber ICDs. In a single-chamber ICD, stimulation pulses are provided to, and cardiac activity is sensed within, a single-chamber of the heart, either the right ventricle or the right atrium. In a dual-chamber ICD, stimulation pulses are provided to, and cardiac activity is sensed within, two chambers of the heart, namely both the right atrium and the right ventricle. The left atrium and left ventricle may also be sensed and paced, provided that suitable electrical contacts are effected therewith.

In general, both single and dual-chamber ICDs are classified by type according to a three letter code. In this code, the first letter identifies the chamber of the heart that is paced (i.e., the chamber where a stimulation pulse is delivered) with a "V" indicating the ventricle, and "A" indicating the atrium, and a "D" indicating both the atrium and the ventricle. The second letter of the code identifies the chamber where cardiac activity is sensed, using the same letters to identify the atrium, ventricle, or both, and where an "O" indicates that no sensing takes place.

The third letter of the code identifies the action or response taken by the ICD. In general, three types of actions or responses are recognized: (1) an Inhibiting ("I") response, in which a stimulation pulse is delivered to the designated chamber after a set period of time unless cardiac activity is sensed during that time, in which case the stimulation pulse is inhibited; (2) a Trigger ("T") response, in which a stimulation pulse is delivered to the designated chamber of the heart a prescribed period after a sensed event; or (3) a Dual ("D") response, in which both the Inhibiting response and Trigger response are invoked, inhibiting in one chamber of the heart and triggering in the other.

A fourth letter, "R", is sometimes added to the code to signify that a particular mode identified by the three letter code is rate-responsive, in which the pacing rate may be adjusted automatically by the ICD, based on one or more physiological factors, such as blood oxygen level or the patient's activity level. As used herein, "(R)", for example, DDD(R), refers to the occurrence of two modes, such as DDD and/or DDDR.

Thus, for example, a DDI pacemaker is capable of sensing and pacing in both chambers, and operates in a non-atrial tracking mode, i.e., it inhibits ventricular stimulation pulses when a prior ventricular activity is sensed.

A DDDR ICD represents a fully automatic ICD that is capable of sensing and pacing in both the atrium and ventricle, and is also capable of adjusting the pacing rate based on one or more physiological factors, such as the patient's activity level. In general, DDD(R) pacing has four functional states: (1) P-wave sensing, ventricular pacing; (2) atrial pacing, ventricular pacing; (3) P-wave sensing, R-sensing; and (4) atrial pacing, R-wave sensing. Advantageously, for the patient with complete or partial heart block, the DDD(R) ICD tracks the atrial rate which is set by the heart's SA node, and then paces in the ventricle at a rate that follows this atrial rate. Because the rate set by the SA node represents the rate at which the heart should beat in order to meet the physiological demands of the body (at least for a heart having a properly functioning SA node), the rate maintained in the ventricle by such an ICD is truly physiologic.

One problem facing the advent of dual-chamber ICDs is that when an ICD delivers a stimulation pulse to the ventricle during an appropriate portion of a cardiac cycle, this pulse may be sensed by the atrial channel. Therefore, it is common practice in the art to apply a post-ventricular atrial blanking ("PVAB") period upon delivery of a ventricular stimulation pulse in order to prevent the saturation of the sense amplifiers of the atrial channel. During a PVAB period all cardiac activity is ignored by the atrial channel. Because ventricular and atrial pulses are sensed through the same lead electrodes through which the stimulation pulses are delivered, the resulting polarization signal, also referred to as an "after potential," formed at the electrodes, may corrupt the evoked response, which is sensed by the sensing circuits. This undesirable situation occurs frequently because the polarization signal may be three or more orders of magnitude greater than the evoked response.

Furthermore, the lead polarization signal is not easily characterized; it is a complex function of the lead materials, lead geometry, tissue impedance, stimulation energy and other variables, many of which are continually changing over time. By disabling the atrial sense amplifier, that is, applying a refractory or "blanking" period upon the delivery of a ventricular stimulating pulse, the atrial sense amplifier is not effected by the ventricular stimulation pulse. At a specified time interval after the delivery of a ventricular stimulating pulse, the atrial sense amplifiers are enabled again to sense intrinsic or evoked atrial events.

However, the PVAB period poses a problem in that it may occur mid-way or even late in the atrial cycle and may therefore result in an inability of the atrial channel to sense the next intrinsic atrial event. Essentially, the atrial channel is "blinded" to rapid atrial rates precluding proper diagnostic and therapeutic measures by the ICD. For example, a missed atrial event could trigger an atrial stimulation pulse to be inappropriately delivered by the ICD or, in ICDs programmed to operate in one of a plurality of operating modes, cause the ICD to inappropriately switch modes. Such inappropriate pacing or sensing could endanger the patient by inducing a sequence of events that might induce cardiac arrhythmias.

Another problem facing the development of dual-chamber ICDs is that the evoked R-wave (the electrical signal associated with ventricular contraction) subsequent to a ventricular stimulation pulse will typically propagate to the atrium in patients with intact atrioventricular ("AV") conduction. This propagated signal of a ventricular R-wave in the atria is commonly referred to as "far-field R-wave" (FFR). Even a premature ventricular contraction ("PVC"), an arrhythmic event common in many patients who require implantable cardiac devices, may propagate and produce a far-field signal on the atrial channel. Such far-field signals sensed by the atrial channel could be interpreted as atrial events. This erroneous sensing could be misinterpreted by the controlling operations of the ICD as a change in atrial rate or even an atrial arrhythmia and consequently invoke improper therapeutic measures, potentially harming the patient.

In order to overcome this risk, the PVAB period employed upon the delivery of a ventricular pulse is commonly programmed long enough to encompass the far-field signal associated with the propagation of a ventricular R-wave subsequent to a ventricular stimulation pulse. This PVAB period is commonly programmed to be a fixed time interval, typically 150 msec. However, this relatively long, fixed PVAB period may exacerbate the limitations of a dual-chamber device in that the ability of the ICD to detect rapid atrial rates may be further impaired. Devices use a rate branch algorithm for SVT discrimination. If the atrial signal is not sensed appropriately, the device could miss diagnose the arrhythmia as VT in stead of SVT and deliver inappropriate therapy.

The window of time that the atrial channel is enabled for sensing atrial events is directly shortened as the PVAB period is lengthened to eliminate far-field signals from being sensed. Furthermore, conduction time between the ventricle and the atrium will vary from patient to patient. In some patients, far-field signals associated with ventricular events may occur even later than the typically programmed 150 msec blanking period. Using still longer blanking periods could more severely impair the ability of the ICD to detect even normal atrial rates.

Maximizing the window of time that the atrial channel is enabled for sensing atrial events is particularly important for ICDs that are programmed to operate in one of a plurality of possible operating modes.

ICDs capable of operating in a plurality of modes are important because, for example, a given patient may develop fast atrial rhythms that result from a pathologic arrhythmia, such as a pathological atrial tachycardia, atrial fibrillation, or atrial flutter. In these cases, a DDD(R) ICD may pace the ventricle in response to the sensed atrial arrhythmia up to a programmed maximum tracking rate ("MTR").

Occasionally it is possible at the time of implantation of an ICD to determine whether an atrial tachycardia, atrial fibrillation, or atrial flutter condition is going to develop. In such instances, the ICD may be programmed to operate in a different mode of operation, the leads may be repositioned within the heart, or other actions may be taken to minimize the likelihood of such pathologic arrhythmias occurring. However, it is not always possible at the time of implantation to determine whether a patient will develop an atrial arrhythmia after the ICD is implanted.

Therefore, if such pathologic arrhythmias subsequently occur, they must be treated using other techniques, such as through the administration of medication, which generally requires the attendance of a physician. However, a physician is not always present when such pathologic arrhythmias develop, and even when a physician is available, such medication also may suppress undesirably the ability of the SA node to increase the sinus rate during periods of exercise, emotional stress, or other physiologic stress. Thus, the use of such medication may prevent the ICD from functioning as an intrinsic physiological rate-responsive pacemaker.

As a result, attempts have been made in the art to prevent undesirable tracking of pathologic atrial arrhythmias by automatically switching the mode of operation of the ICD from an atrial tracking pacing mode to a non-atrial tracking pacing mode. For example, an atrium-controlled ICD has been described, wherein the ICD temporarily switches from an atrial tracking mode to a non-atrial tracking mode for a fixed number of stimulation pulses if the sensed atrial activity indicates an atrial arrhythmia may be developing.

Additionally, an atrial tracking ICD with automatic mode switching capability has been disclosed. This ICD has the capability of setting a tachycardia rate limit ("TRL") or tachycardia detection rate ("TDR") slightly above an MTR, so that mode switching to a non-atrial tracking mode occurs when the TRL or TDR is exceeded. A third threshold rate is also set at a value below the MTR. The ICD switches back to an atrial tracking mode when the patient's atrial rate drops below this third threshold. To avoid mode switching based on a single short atrial interval between atrial events, the atrial rate is continuously averaged over several cycles. This technique effectively prevents frequent mode switches in patients whose atrial rates "hover" around the MTR.

Also described is an implantable dual-chamber ICD programmed to operate primarily in an atrial tracking mode. This ICD automatically switches its mode of operation from the atrial tracking mode to a non-atrial tracking mode in the event a filtered atrial rate exceeds a prescribed upper rate limit. This mode switching is accompanied by a corresponding switching from a primary set of operational parameter settings for the primary mode, to an alternate set of operational parameters for the alternate mode.

One parameter shared by mode-switching algorithms that cause the ICD to switch from atrial tracking mode to a non-atrial tracking mode is a step that monitors events sensed by the atrial channel to determine whether a pathologic arrhythmia has occurred such that the mode-switching algorithm should be invoked. Thus it would be desirable to provide a system and method for automatically adjusting the post-ventricular atrial blanking period such that the blanking period following a ventricular stimulation pulse is minimized, thereby allowing the longest atrial sensing window possible in a mode-switching ICD. Furthermore, it would be desirable to implement the system and method in a way that allows far-field signals sensed by the atrial channel to be properly interpreted as the ventricular events that they are associated with, thereby excluding them from atrial rate determinations. It would further be desirable to enable the ICD to perform this automatic PVAB period adjustment without requiring dedicated circuitry and/or special sensors.

SUMMARY OF THE INVENTION

Briefly, and in general terms, the invention relates to methods and devices involving automatic atrial blanking, whereby blanking periods are associated with post-ventricular relative atrial refractory periods based on the timing occurrences of atrial detections. The number and location of blanking windows may be automatically updated, on a beat-by-beat basis or periodically.

In one aspect, during a period of time comprising a plurality of cardiac cycles, a relationship between ventricular events and atrial detections is established. Based on the relationship, a post-ventricular atrial refractory period is defined. The period includes an absolute atrial refractory period and a segmented relative atrial refractory period, wherein the segmented relative atrial refractory period includes at least one blanking window during which atrial detections of ventricular events have or are likely to occur.

In another aspect of the invention, time data for ventricular events and atrial detections is acquired. The acquired time data is processed to establish time relationships between a first ventricular event and each atrial detection that occurs prior to a subsequent ventricular event. Time relationships are monitored over time to identify atrial detections corresponding to atrial detections of ventricular events, which are then ignored for purposes of atrial rate calculations.

BRIEF DESCRIPTION OF THE DRAWINGS

Further features and advantages of the present invention may be more readily understood by reference to the following description taken in conjunction with the accompanying drawings, in which:

FIGS. 7A-7D are a series of data buffers illustrating an exemplary timing data acquisition process;

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout. For illustration purposes, the ICD will be described in terms of a dual-chamber ICD having a plurality of selectable modes of operation, including a primary mode and an alternate mode and which is programmed and implanted in a patient with intact AV conduction.

Figure 1:
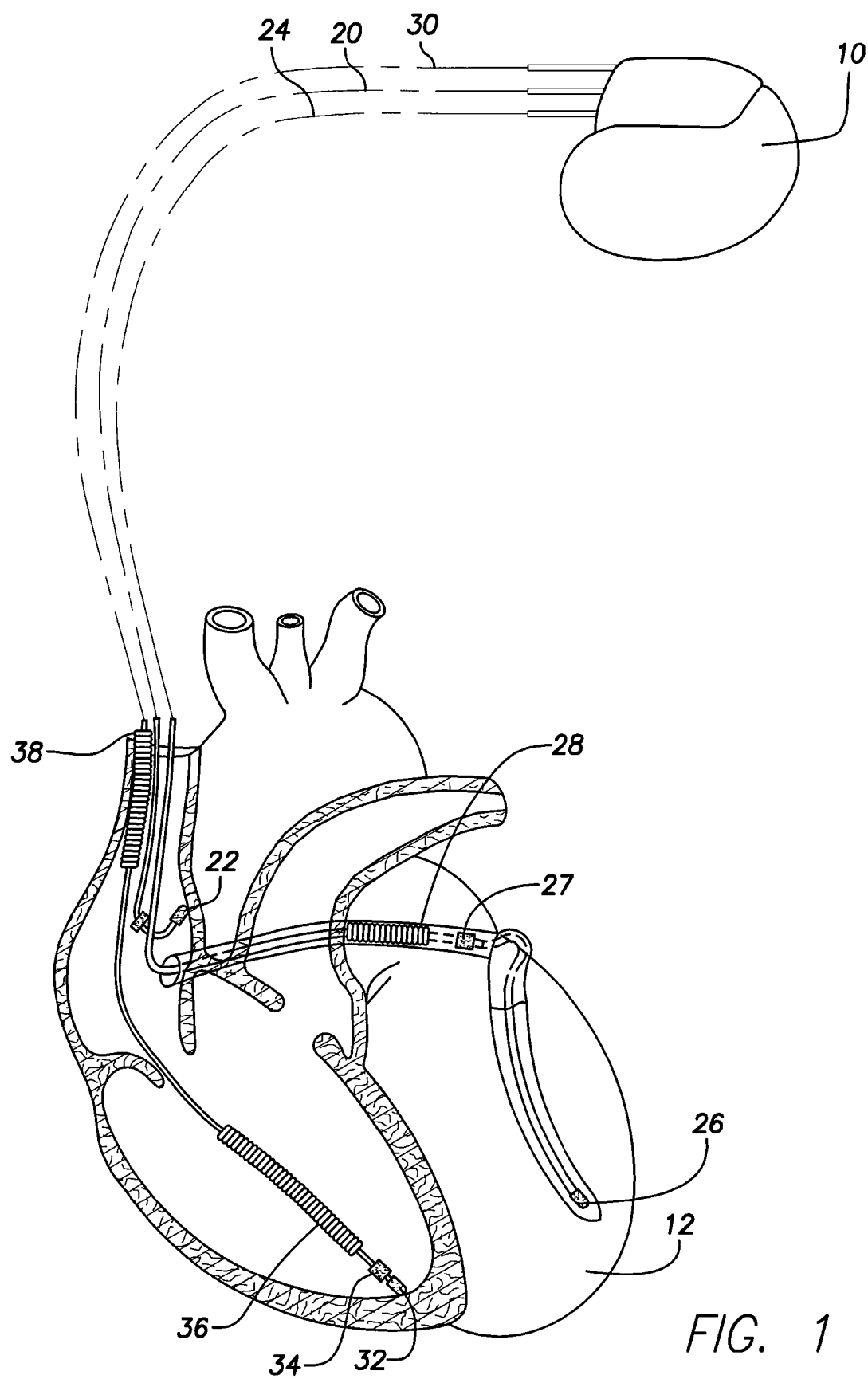
FIG. 1 is a simplified diagram illustrating an implantable cardiac device in electrical communication with at least three leads implanted into a patient's heart for monitoring cardiac signals.

As shown in FIG. 1, there is a stimulation device 10 in electrical communication with a patient's heart 12 by way of three leads, 20, 24, and 30, suitable for delivering multi-chamber stimulation shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to retrieve atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28.

The ICD 10 is also shown in electrical communication with the patient's heart 12 by way of an implantable ventricular lead 30 having, in this embodiment, a right ventricular tip electrode 32, a right ventricular ring electrode 34, a right ventricular ("RV") coil electrode 36, and a superior vena cava ("SVC") coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the SVC. Accordingly, the right ventricular lead 30 is capable of receiving cardiac signals and delivering stimulation in the form of pacing and shock therapy to the right ventricle.

Figure 2:
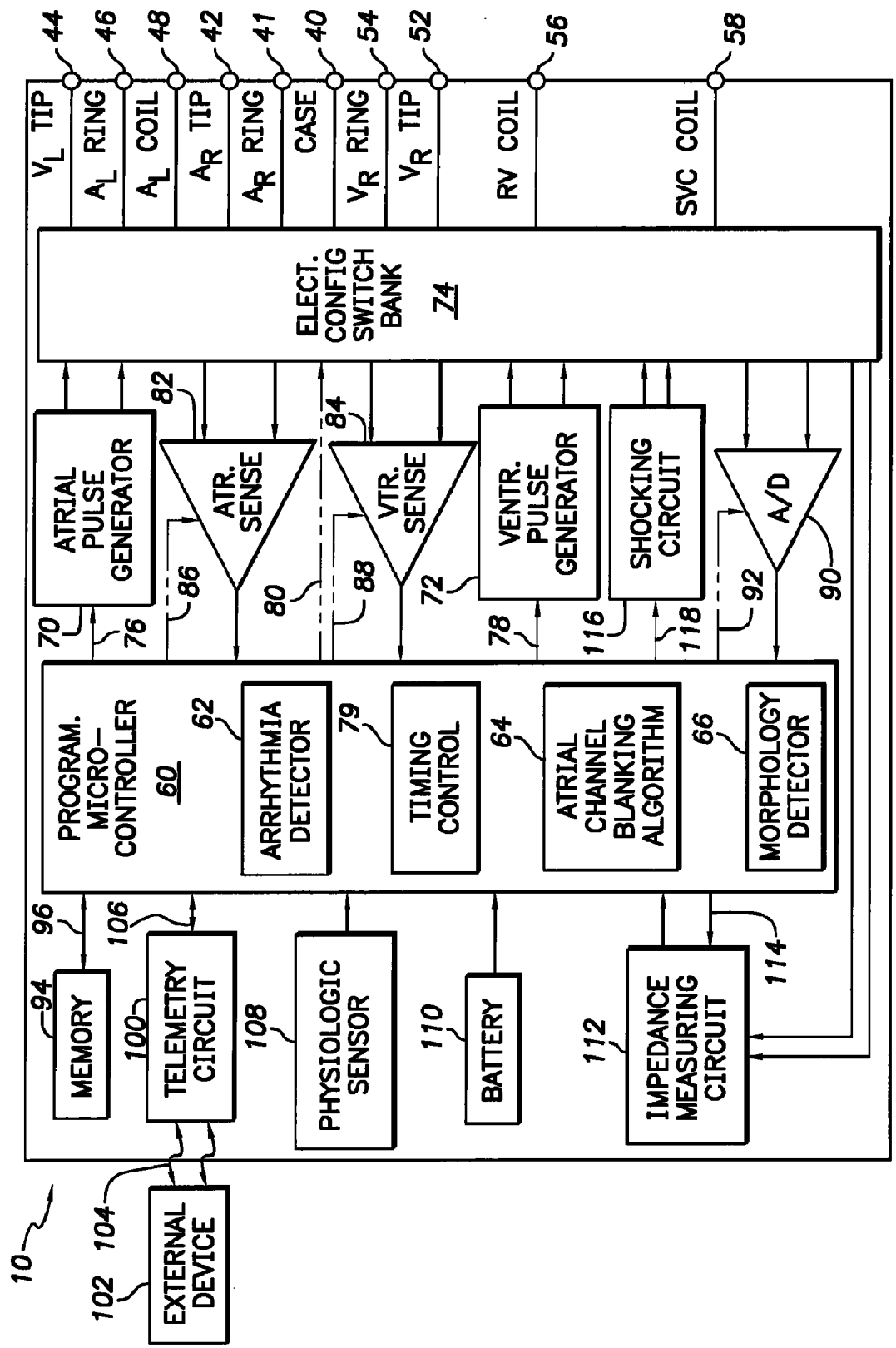
FIG. 2 is a functional block diagram of the device of FIG. 1 illustrating the basic elements of a cardiac device that may be configured to sense conditions and deliver therapy.

As illustrated in FIG. 2, a simplified block diagram is shown of the multi-chamber ICD 10, which is capable of operating in one of a plurality operating modes and capable of treating both fast and slow arrhythmias with stimulation therapy, including cardioversion, defibrillation, and pacing stimulation. While a particular multi-chamber device is shown, this is for illustration purposes only, and one of ordinary skill in the art could readily duplicate, eliminate or disable the appropriate circuitry in any desired combination to provide a device capable of treating the appropriate chamber(s) with cardioversion, defibrillation, and pacing stimulation.

The housing 40 for the stimulation device 10, shown schematically in FIG. 2, is often referred to as the "can," "case" or "case electrode" and may be programmably selected to act as the return electrode for all "unipolar" modes. The housing 40 may further be used as a return electrode alone or in combination with one of the coil electrodes, 28, 36, and 38, for shocking purposes. The housing 40 further includes a connector (not shown) having a plurality of terminals, 41, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial tip electrode 22.

To achieve left chamber sensing, pacing, and shocking, the connector includes at least a left ventricular tip terminal 44, a left atrial ring terminal 46, and a left atrial shocking terminal 48, which are adapted for connection to the left ventricular tip electrode 26, to the left atrial tip electrode 27, and the left atrial coil electrode 28, respectively.

To support right chamber sensing, pacing, and shocking, the connector further includes a right ventricular tip terminal 52, a right ventricular ring terminal 54, a right ventricular shocking terminal 56, and a SVC shocking terminal 58, which are adapted for connection to the right ventricular tip electrode 32, right ventricular ring electrode 34, a RV coil electrode 36, and the SVC coil electrode 38, respectively.

At the core of the ICD 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller may be used to carry out the functions described herein. The use of the microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via switch bank 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing circuitry 79, which is used to control the timing of stimulation pulses (e.g., pacing rate atrial-ventricular (AV) delay, atrial interconduction (A-A) delay, pause durations of ventricular interconduction (V-V) delay, etc.) as well as to keep track of timing of refractory periods, blanking periods, noise detection windows, evoked response windows, alert intervals, marker channel timing, etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20 through the switch bank 74 for detecting the presence of cardiac activity in each of the four chambers of the heart. Accordingly, the atrial and ventricular sensing circuits, 82 and 84, may include dedicated sense amplifiers, multiplexed amplifiers or shared amplifiers. The switch bank 74 determines the "sensing polarity" of the cardiac signal by selectively closing the appropriate switches, as is known in the art. In this way, the clinician may program the sensing polarity independent of the stimulation polarity.

Each sensing circuit, 82 and 84, preferably employs one or more low power, precision amplifiers with programmable gain and/or automatic gain control, band pass filters, and a threshold detection circuit, as is known in the art, to selectively sense the cardiac signal of interest. The automatic gain control enables the ICD 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, respectively, in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 84, as is known in the art.

For arrhythmia detection, the device 10 utilizes the atrial and ventricular sensing circuits, 82 and 84, to sense cardiac signals to determine whether a rhythm is physiologic or pathologic as processed by an arrhythmia detector 62. As used herein "sensing" is reserved for the noting of an electrical signal, and "detection" is the processing of the sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Additionally, the arrhythmia detector 62 is programmed with an algorithm responsible for automatic mode-switching.

Numerous mode-switching algorithms are known to those skilled in the art and will not be described in detail herein. Preferably, the ICD 10 has a plurality of selectable modes of operation, including a primary mode and an alternate mode. When operating in a primary mode, the ICD of the present invention operates according to a primary set of operational parameters, including a primary pacing rate and when operating in an alternate mode, the ICD operates according to an alternate set of operational parameters, including an alternate pacing rate. Programming ICDs to operate in primary and alternate modes of operation is well known to those of skill in the art. More preferably, the mode-switching algorithm is programmed to provide the ICD 10 with the capability of switching from a primary atrial tracking mode to an alternate non-atrial tracking mode if a pathologic atrial arrhythmia is detected, such as atrial tachycardia, atrial fibrillation, and atrial flutter.

The mode-switching algorithm preferably also is programmed to switch back to the primary mode once the pathologic arrhythmia subsides. As further explained below, the microcontroller 60 further includes an atrial channel blanking algorithm 64 which works in concert with the mode-switching algorithm of the arrhythmia detector 62. In one embodiment, the primary mode of operation for the ICD may include DDD, DDDR, VDD, VDDR, DDT, and DDTR modes of operation. Additionally, the alternate mode of operation for the ICD may include DDI, DDIR, VDI, DDT, and DDTR modes. The system and method of the present invention are not to be limited by the type of mode-switching algorithm employed by the ICD, or the particular primary and secondary modes of operation employed by the ICD.

In one embodiment, the ICD 10 uses a filtered atrial rate ("FAR") as a basis for mode-switching in order to reduce mode-switching responses due to, for example, electrical noise or aberrant P-waves. The FAR may be obtained by filtering the intrinsic atrial rate using a rate smoothing filter subroutine. The rate smoothing filter subroutine generates the FAR during each cycle by limiting the amount by which the FAR may change from cycle to cycle. If the FAR exceeds a predetermined upper rate limit, referred to as an atrial tachycardia detection rate ("ATDR"), a pathological atrial arrhythmia is deemed to exist, and the ICD 10 automatically switches from its primary mode of operation to an alternate mode of operation. Mode-switching according to FAR is well known in the art and will not be described further herein.

Cardiac signals are also applied to the inputs of an analog-to-digital (A/D) data acquisition system 90. The data acquisition system 90 (also referred to herein as a "sampler") is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes. Additionally, the data acquisition system 90 is coupled to the microcontroller 60 via signal line 92.

Advantageously, the data acquisition system 90 may be coupled to the microcontroller 60, or other detection circuitry, such as the arrhythmia detector 62, for detecting and sensing events that may be classified as either physiologic or pathologic.

As may be noted in FIG. 2, the microcontroller 60 further includes a morphology detector 66. Morphology detection is well known in the art and may be employed for discerning T-wave morphology, fully paced ventricular beats, intrinsic ventricular activation or ventricular fusion, atrial loss of capture, an atrial evoked response, or an atrial fusion beat. The morphology detector 66 may utilize the signals provided by the acquisition system 90.

The microcontroller 60 is coupled to the memory 94 by a suitable data/address bus 96. In addition to internal cardiac signals, the memory 94 may store programmable operating parameters used or modified by the microcontroller 60, as required, in order to control the operation of the ICD 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy.

Advantageously, initial operating parameters of the implantable device 10 may be non-invasively programmed into the memory 94 through a telemetry circuit 100 in telemetric communication with an external communication device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through the established communication link 104. In a preferred embodiment, the stimulation device 10 further includes a physiologic sensor 108, commonly referred to as a "rate-responsive" sensor because it is typically used to adjust pacing stimulation rate according to the exercise state or other physiological stress of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV delay, V-V delay, etc.) at which the atrial and ventricular pulse generators, 70 and 72, generate stimulation pulses.

The stimulation device 10 additionally includes a battery 110, which provides operating power to all of the circuits shown in FIG. 2. For the implantable device 10 to employ shocking therapy, the battery must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries, as is true for most (if not all) such devices to date. The implantable device 10 further includes magnet detection circuitry (not shown) coupled to the microcontroller 60. The magnet detection circuitry detects whether a magnet is placed over the stimulation device, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the implantable device 10 is shown as having an impedance measuring circuit 112, which is enabled by a control signal 114. The impedance measuring circuit 112 has many known uses. However, it is not critical to the present invention and is therefore shown only for completeness.

If it is the primary function of the device 10 to function as an implantable cardioverter/defibrillator device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV coil electrode 36, or as part of a split electrical vector using the SVC coil electrode 38 or the left atrial coil electrode 28 (i.e., using the RV coil electrode as common).

Cardioversion shocks are generally considered to be of low to moderate energy level (so as to minimize pain felt by the patient), and/or synchronized with a R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In accordance with the invention, automatic mode switching in response to pathologic atrial arrhythmias is improved by preventing or significantly minimizing the use of non-atrial events in atrial rate calculations. This improvement is provided by the inclusion of one or more atrial channel blanking periods or windows of time during the relative period of the post-ventricular atrial refractory period (PVARP). Any signals sensed by the atrial channel during these "blanking periods" are ignored by the mode switching algorithm of the arrhythmia detector 62. Various techniques and processes for including blanking windows within the post-ventricular relative atrial refractory periods are described herein. The techniques are premised on the general observation that non-atrial events detected in the atrium, such as far-field R waves, tend to be very repeatable in their timing relationship with respect to their preceding ventricular event, whereas true atrial events, such as P waves, tend not to have a strong time correlation with their preceding ventricular event.

Figure 3:
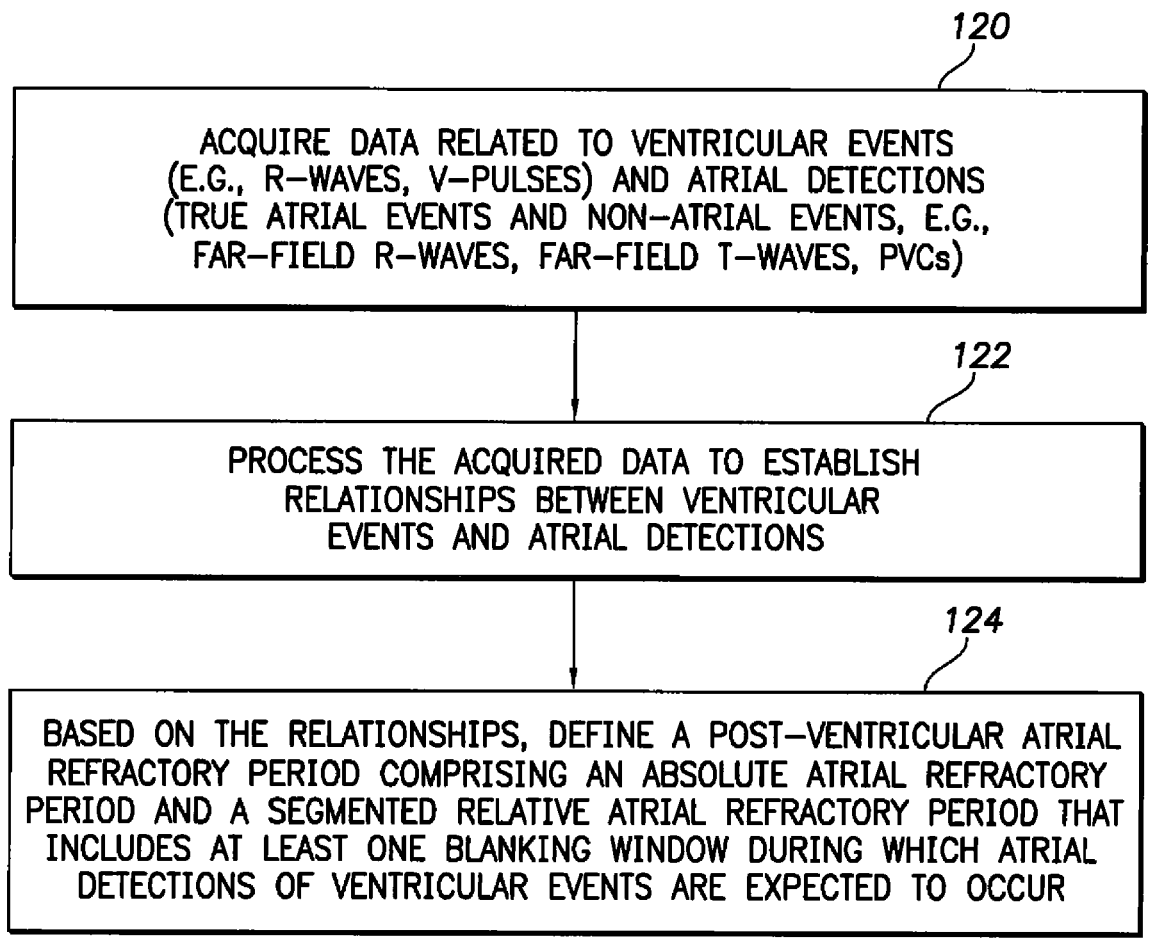
FIG. 3 is a flow diagram for defining a post-ventricular atrial refractory period including a segmented relative atrial refractory period with one or more blanking windows.

In general terms and with reference to FIG. 3, such techniques include acquiring time data related to ventricular events and atrial detections that occur between ventricular events (block 120). As used herein "ventricular events" correspond to intrinsic ventricular depolarizations (R waves) and ventricular stimulation pulses. R waves are sometimes referred to as "R senses", while ventricular stimulation pulses are at times referred to as "V-paces." "Atrial detections" correspond to true atrial events, such as intrinsic atrial depolarizations (P waves), as well as non-atrial events. "Non-atrial events," also referred to herein as "atrial detections of ventricular events" correspond to signals sensed in an atrium having an origin in the ventricle and may include far-field R waves, far-field T waves and premature ventricular contractions (PVCs).

Continuing with FIG. 3, techniques of the present invention further include processing the acquired data to establish relationships between ventricular events and atrial detections (block 122) and based on the relationships, defining a post-ventricular atrial refractory period made up of an absolute atrial refractory period and a segmented relative atrial refractory period that includes at least one blanking window during which non-atrial events, i.e., atrial detections of ventricular events occur (block 124).

Figure 4:
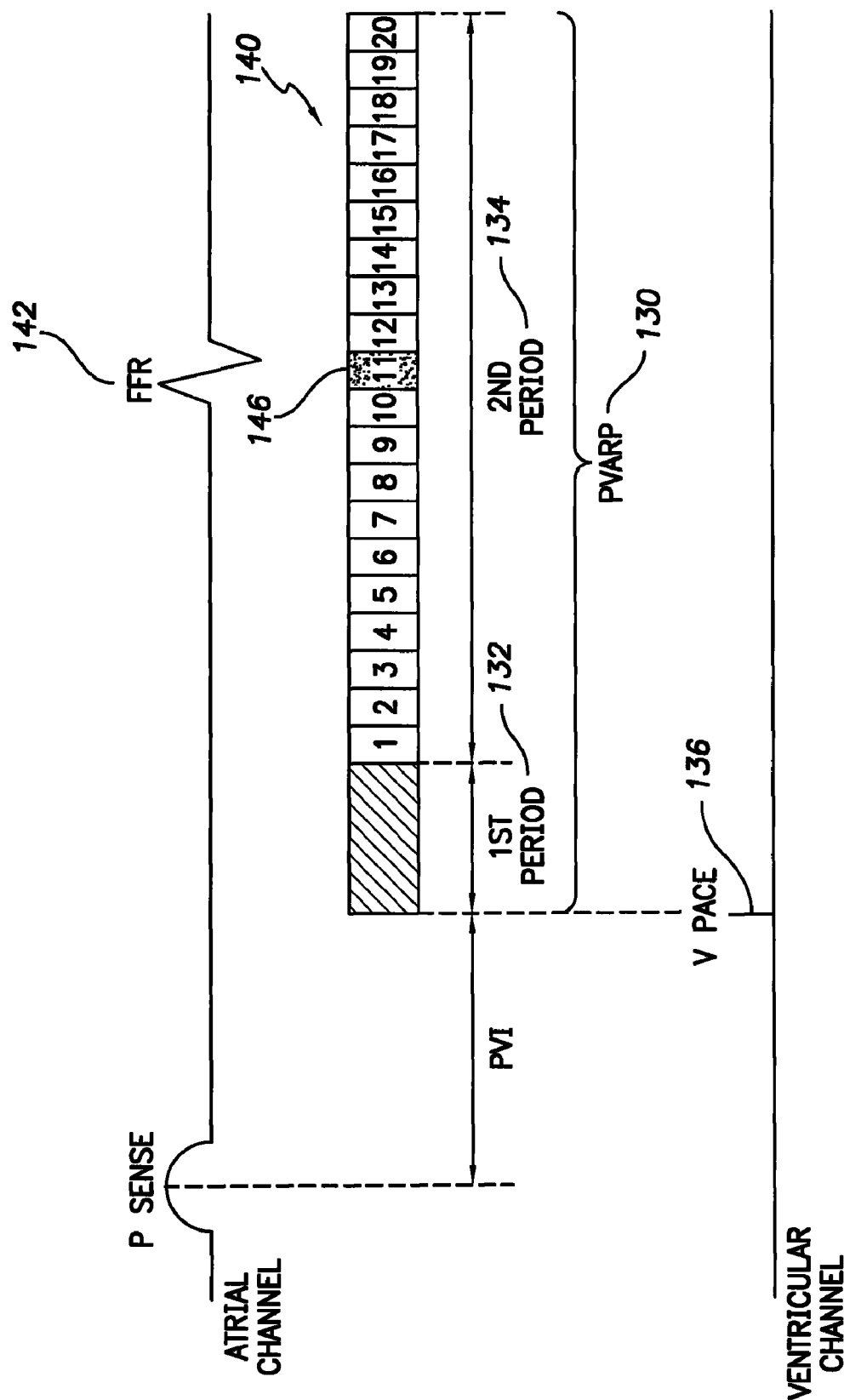
FIG. 4 is a timing diagram of an atrial channel and a ventricular channel illustrating a post-ventricular atrial refractory period including a segmented relative atrial refractory period with one blanking window following a ventricular stimulation pulse (V pace)
Figure 5:
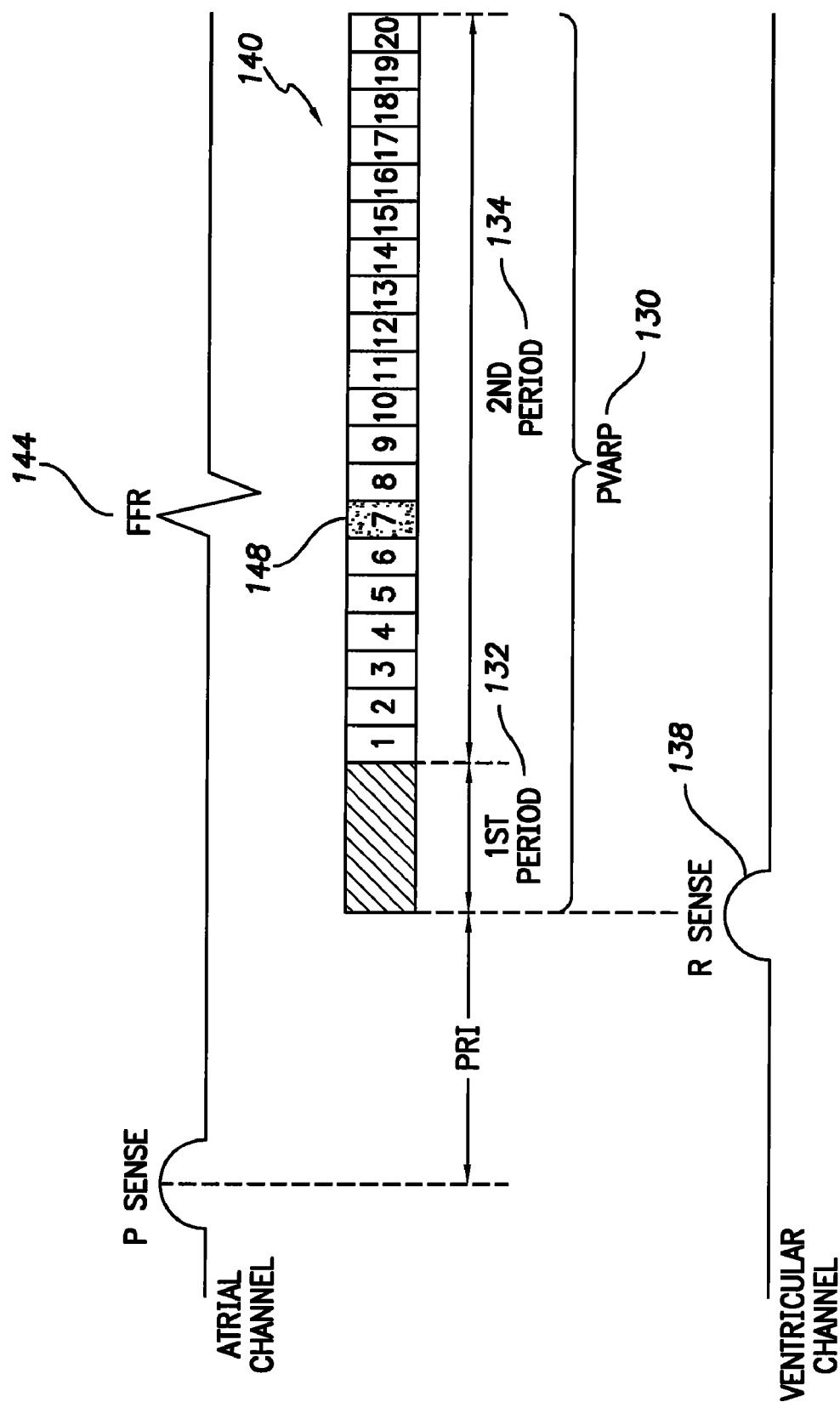
FIG. 5 is a timing diagram of an atrial channel and a ventricular channel illustrating a post-ventricular atrial refractory period including a segmented relative atrial refractory period with one blanking window following a ventricular sensed event (R sense)

With reference to FIGS. 4 and 5, a post-ventricular atrial refractory period 130 implemented in accordance with the invention includes a first period 132 and a second segmented period 134. The first period 132 corresponds to an absolute atrial refractory period. This period 132 is typically initiated upon delivery of a ventricular pacing stimulus 136 (FIG. 4) by a ventricular pulse generator or upon the sensing of an intrinsic ventricular event 138 (FIG. 5), such as an R-wave, by a ventricular sense channel. During the first period 122, i.e., the absolute atrial refractory period, all activity is ignored by the atrial sense channel 82 (FIG. 2). This is done, for example, by disabling the atrial sense amplifier.

The segmented second period 134 follows the first period 132 and generally corresponds to a relative atrial refractory period. During this period 134, the atrial sense channel is responsive to sensed signals, but the sensed signals are not used for the purposes of resetting pacing timing cycles or tracking of the sensed atrial signals. They are instead used for example, for computing a filtered atrial rate for purposes of automatic mode switching. This period may, however, include one or more atrial channel blanking windows 146, 148. Any atrial detection—whether it is a true atrial event or a non-atrial event—that occurs during a blanking window is ignored for purposes of atrial rate calculation. Thus, in accordance with the invention, the segmented relative atrial refractory period includes segments where atrial detections are used for atrial rate calculations and other segments where atrial detections are ignored for such purposes.

Figure 6:
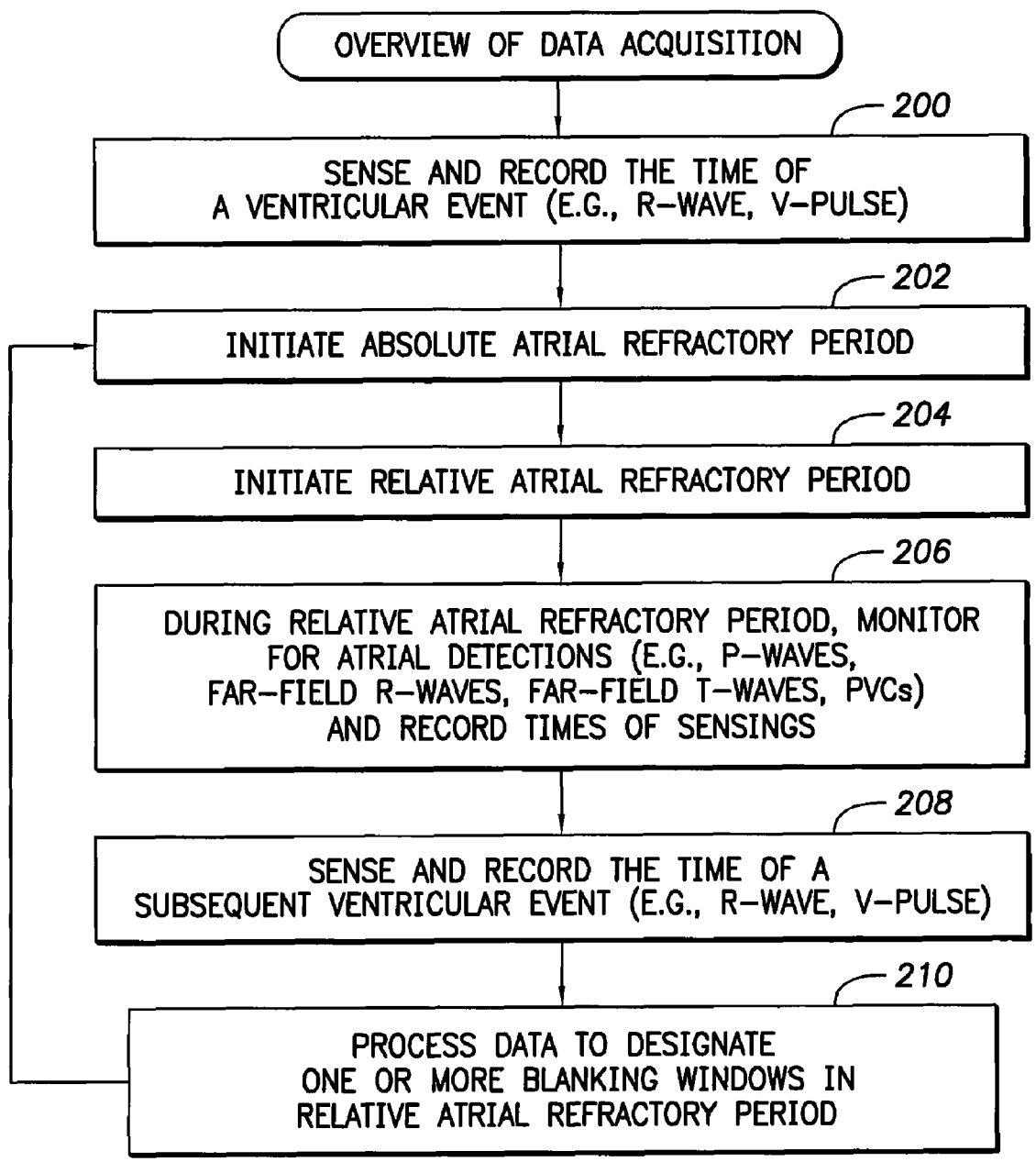
FIG. 6 is a flow diagram for acquiring timing data related to ventricular events and atrial detections.

With reference to FIG. 6, an exemplary process for acquiring data to be used in implementing a segmented post-ventricular relative atrial refractory period 134 (FIG. 5) includes sensing and recording the time of a ventricular event 138 (block 200). Upon detection of a ventricular event, an absolute atrial refractory period 132 is initiated (block 202), followed by the initiation of a relative atrial refractory period 134 (block 204). During the relative atrial refractory period 134, the atrial sense channel is monitored for atrial detections and the times of these detections are recorded (block 206). Upon sensing and recording the time of a subsequent ventricular event (block 208), the data is processed to designate one or more blanking windows 148 in the segmented relative atrial refractory periods 134 (block 210). The process then returns to collect additional data (block 202) for the ventricular event detected at block 208 and the process is repeated.

The data acquisition process of FIG. 6 may be implemented using an event timer that measures the time relationships between ventricular events and atrial detections. In one exemplary configuration, the event timer may be an 8-bit timer that runs at a clock setting of 7.8 milliseconds per count. The event timer resets upon sensing an atrial event, which may be either an intrinsic P wave or an atrial pulse. With reference to FIGS. 7A-7D, a buffer may be used in conjunction with the timer to record event type, such as R-wave, V-pace, P-sense and time of event ("T"), wherein a "P-sense" may correspond to an atrial detection of a ventricular event, or a true atrial event, such as an atrial depolarization (P-wave) or atrial stimulation pulse (P-pace). In one configuration, the buffer is an N entry, 2 byte wide buffer, where 12 is a nominal value for N.

In FIG. 7A, the buffer is reset to start a new cardiac cycle, wherein one cycle corresponds to the time between consecutive ventricular events. In one embodiment, the buffer is reset prior to expiration of the PVARP following a ventricular event. When the buffer is reset the contents of the event timer at the time of the most recent ventricular event is stored in the first location of the buffer along with an 'R' or 'V' event type to identify the start of a new cycle. Thereafter, as shown in FIG. 7B, each time an atrial detection occurs inside the relative atrial refractory period, the current value of the event timer is stored into the next available location in the buffer with a P-sense event type.

With reference to FIG. 7C, when a subsequent ventricular event occurs, the current value of the event timer is saved into the buffer and the type of ventricular event is saved, thus ending the current cycle. The buffer is then reset as shown in FIG. 7D, wherein the contents of the event timer at the time of the most recent ventricular event (last entry of FIG. 7C) is stored in the first location of the buffer along with an 'R' or 'V' event type to identify the start of a new cycle.

Figure 8:
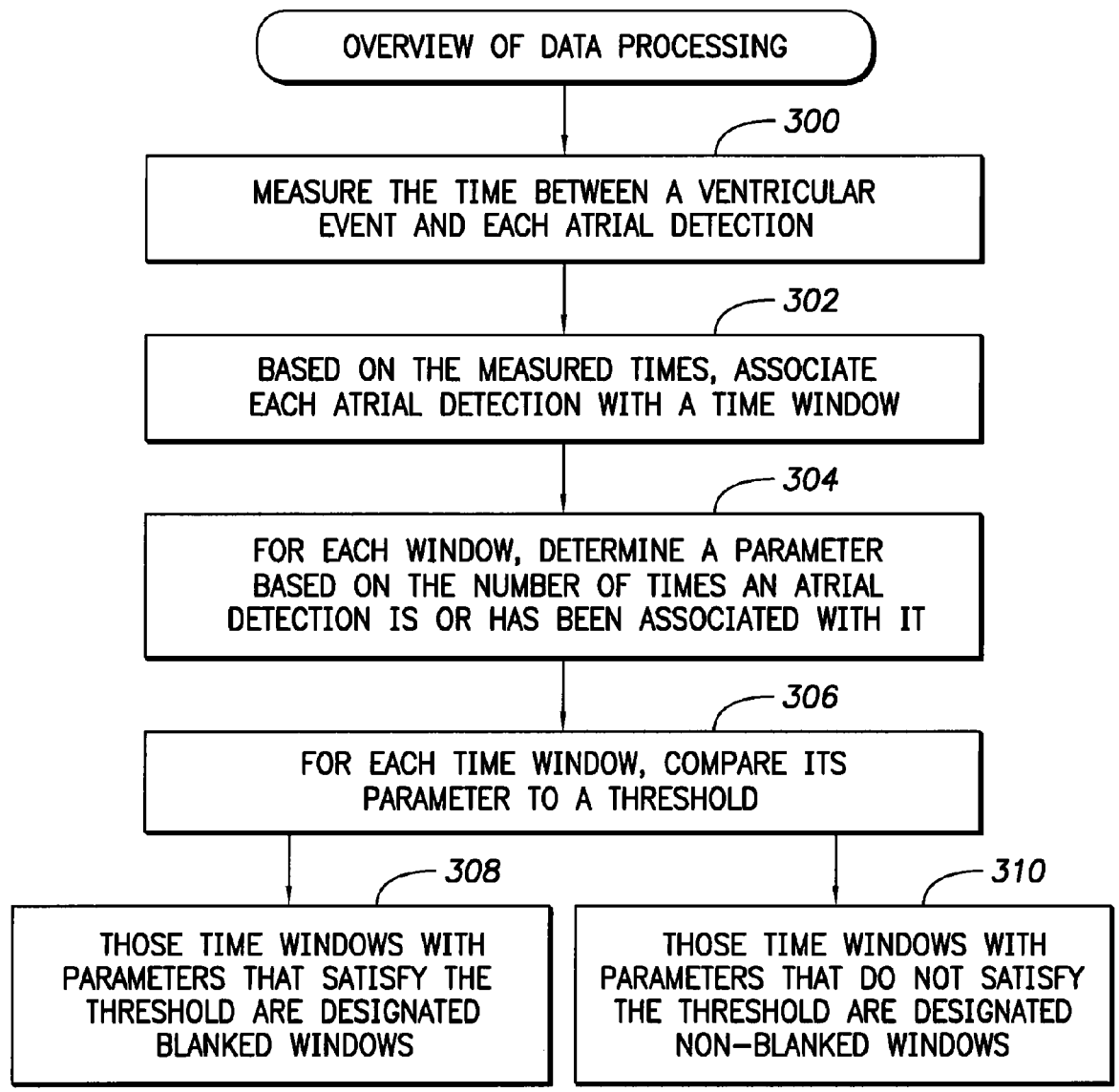
FIG. 8 is a flow diagram for processing acquired timing data to designate blanking periods or windows within a post ventricular relative atrial refractory period.

With reference to FIG. 8, an exemplary technique for processing data acquired by the process of FIG. 6 includes, measuring the time between a ventricular event and each atrial detection (block 300). Based on the measured times, each atrial detection is associated with a time period or time window (block 302). For example, with reference to FIG. 4, far-field R wave 142 occurs within the time window 146 and would therefore be associated with it, while the far-field R wave 144 of FIG. 5 would be associated with another time window 148.

Returning to FIG. 8, a parameter based on the number of times an atrial detection is or has been associated with a particular time window is determined for each window (block 304). As described further below, in some process configurations, the parameter may be a count of the number times an atrial detection falls within a time window. In other configurations, the parameter may be percentage of time atrial detections fall within a time window over a period of time or a running average of atrial detections per time window.

Next, the parameter for each time window is compared to a threshold (block 306). Those time windows with parameters that satisfy the threshold are designated blanking windows (block 308) and the signals within those windows are ignored for purposes of atrial rate calculations. For example, with reference to FIG. 4, assuming far-field R wave 142 repeatedly occurred within time window 146 such that its count parameter satisfies the threshold, then time window 146 would be designated a blanking window. Accordingly, the far-field R wave 142, and any signals sensed during that window 146 during subsequent cardiac cycles, would not be used to compute a filtered atrial rate for purposes of automatic mode switching. However, atrial detections during any blanked windows continued to be acquired (per FIG. 6) and processed (per FIG. 8) for subsequent segmented post-ventricular relative atrial refractory period implementations.

Continuing with FIG. 8, those time windows with parameters that do not exceed the threshold are designated non-blanking windows (block 310). Signals sensed by the atrial sense channel during these windows are categorized as true atrial events and are available for evaluation by the mode-switching algorithm of the arrhythmia detector 62 (FIG. 2).

Figure 9:
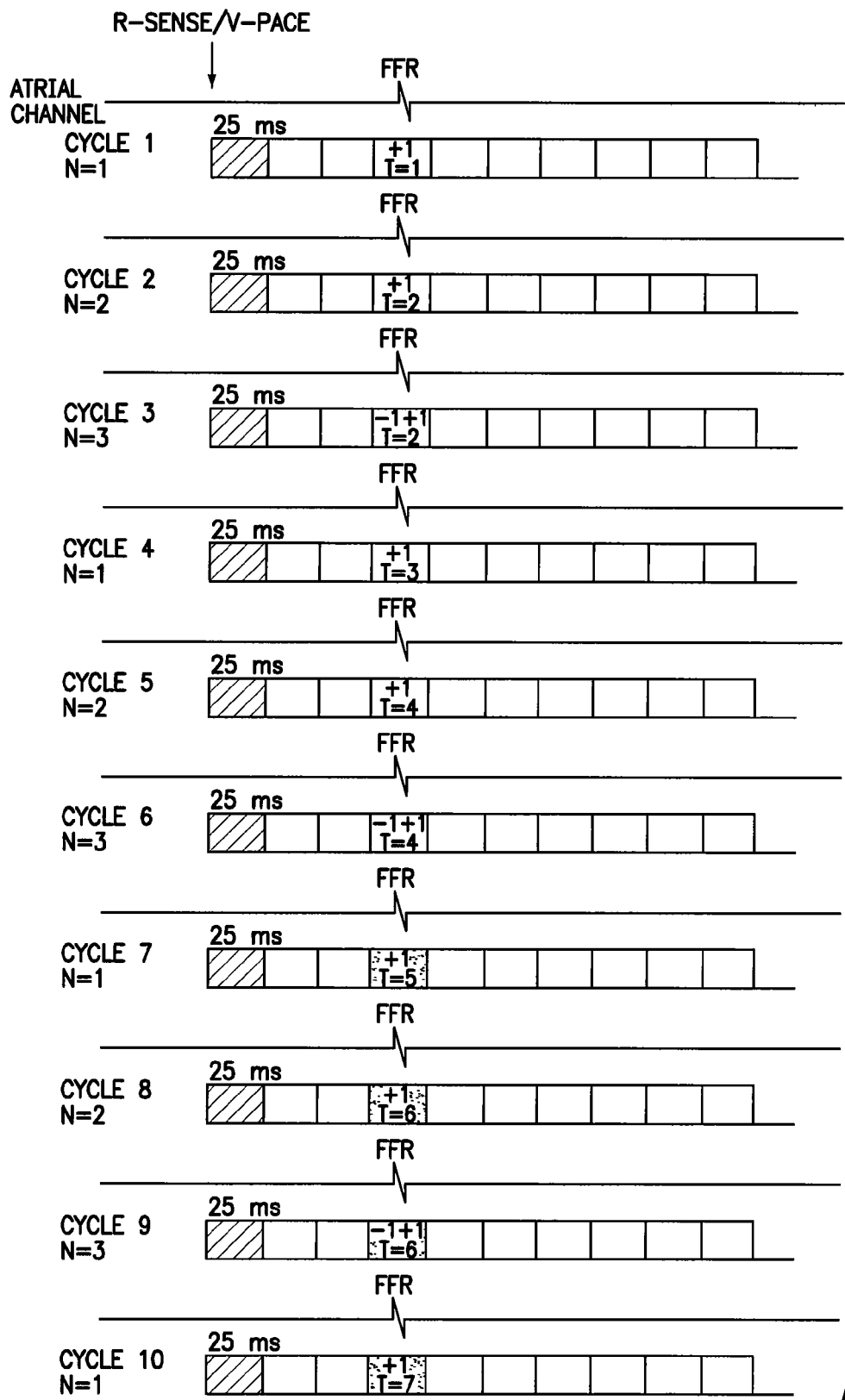
FIG. 9 is a series of timing diagrams of an atrial channel sensing atrial detections (e.g. far-field R waves) over a number of cardiac cycles and illustrating an exemplary count algorithm wherein a window within a segmented relative atrial refractory period becomes blanked based on the repetitive time occurrence of the atrial detections.

With reference to FIG. 9, in one exemplary data processing implementation wherein the parameter is a count, the window designation process operates using the following parameters and rules: a count threshold of 5; a maximum count of 7; at every third ventricular event N, all counts T are decremented by 1. The value of N is decremented by 1 every third cycle, which has the effect of zeroing timing windows in which only true atrial activity is sensed so they are not designated blanking windows.

Accordingly, assuming a far-field R wave (FFR) is detected during each of cycles 1 through 10 at approximately the same time, each far-field R wave would be associated with the third time window after a 25 millisecond absolute atrial refractory period. At cycle 1, ventricular event N=1 and count T=1. At cycle 2, N=2 and T=2. At cycle 3, T would be incremented 1, but because N=3, T is also decremented 1 and thus remains 2. At each cycle, T is compared to the count threshold of 5 and if T satisfies the threshold, e.g., is equal to or greater than the threshold, the third window is blanked—meaning the signal sensed during that window is considered an atrial detection of a ventricular event and is not used for atrial rate calculations. If the count does not satisfy the threshold the signal is considered a true atrial event and is used for atrial rate calculations. This counting and comparing process continues for each cycle. At cycle 7, T=5; accordingly the third window is blanked. For each of cycles 8 through 10, T remains greater than the count threshold and the third window remains blanked. Although the algorithm is designed to blank a particular timing window if its associated count T is equal to or exceeds 5, the counter T has a maximum value of 7 so that a subsequent intermittent loss of detection of far-field events, which will result in the T count decrementing, will not cause the T count to immediately decrement below the threshold.

Figure 10:
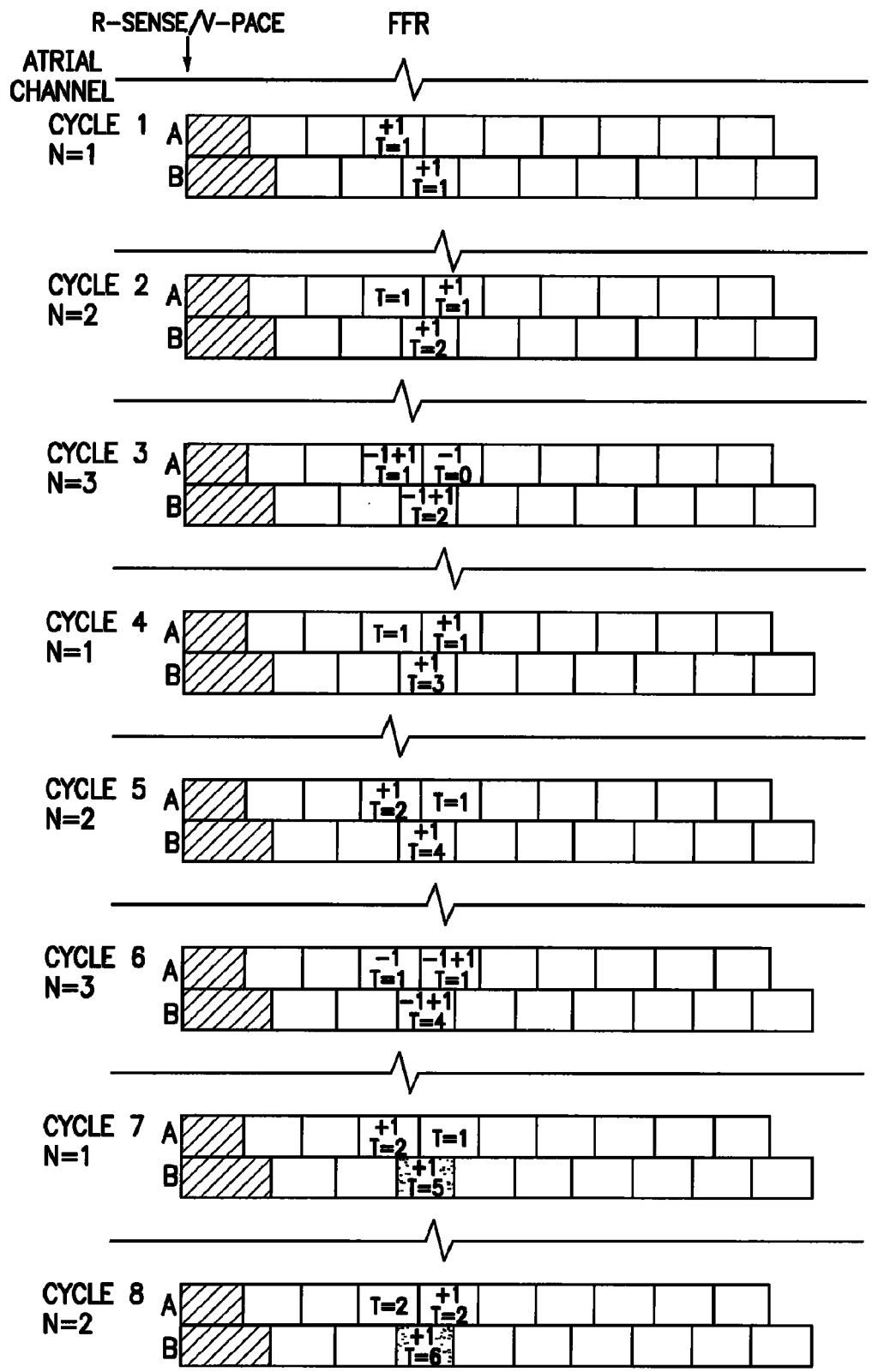
FIG. 10 is a series of timing diagrams of an atrial channel sensing atrial detections (e.g. far-field R waves) over a number of cardiac cycles and illustrating an exemplary count algorithm wherein one window within one of two overlapping segmented relative atrial refractory periods becomes blanked based on the repetitive time occurrence of the atrial detections.

With reference to FIG. 10, in another exemplary data processing implementation operating under the same rules and parameters of FIG. 9, a second count is provided by a second event timer. In this case, the start of the second event timer is delayed relative to the first timer so as to provide sets of overlapping time windows for improved accuracy in identifying far-field signals that very slightly in time from cycle to cycle. For example, assuming the timing of a far-field R wave (FFR) varies from cycle to cycle such that—with respect to window set A—it is associated with a first time window on odd numbered cycles and a second time window adjacent the first time window on even numbered cycles. Because of this, the counts T associated with the third and fourth time windows of window set A would never exceed the threshold count of 5. However, because of the overlapping window set B, the FFR consistently falls within the third time window of window set B. Accordingly, the counts associated with the third window of window set B satisfy the threshold count at cycle 7 and thus the third window would be blanked.

Figure 11:
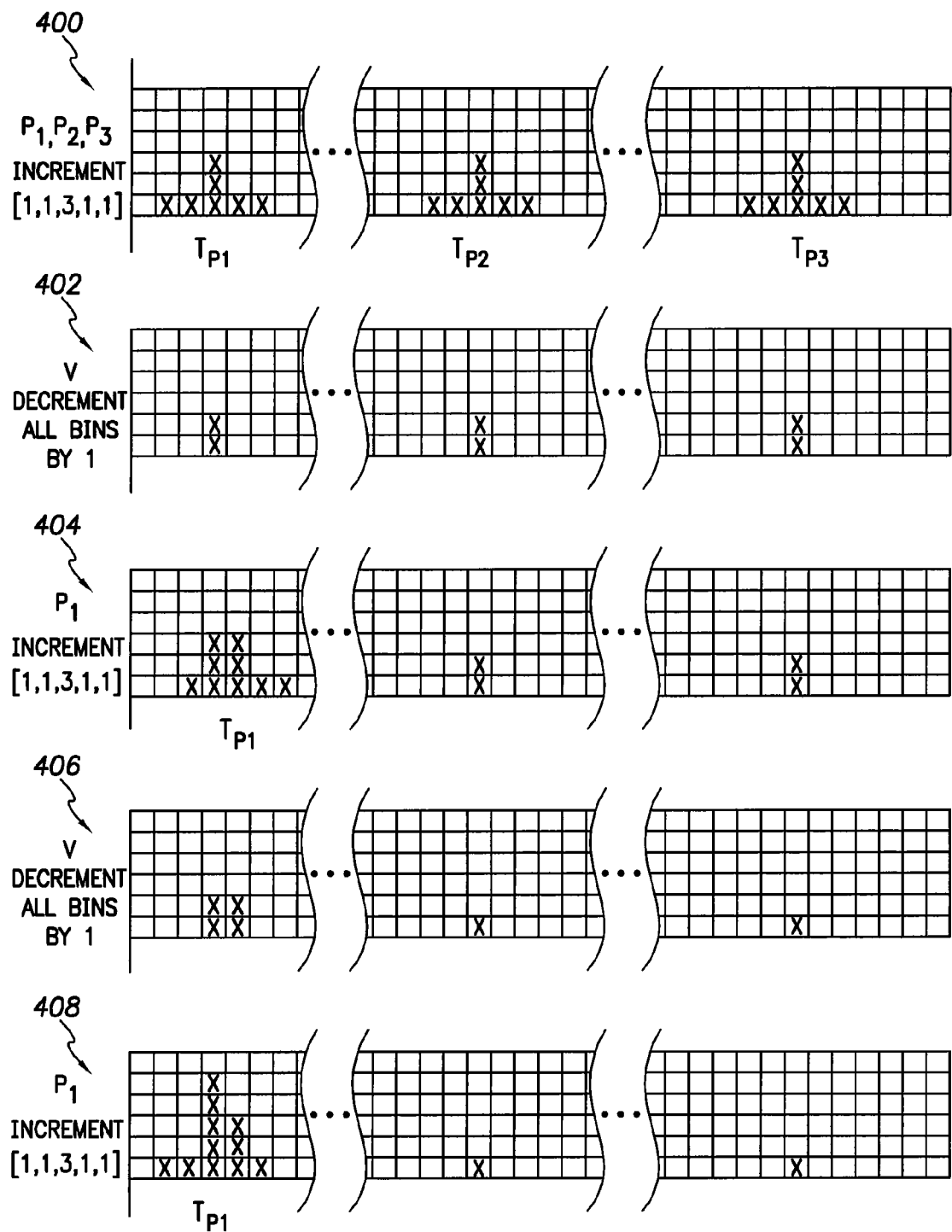
FIG. 11 is a series of histograms with bins corresponding to time windows within a segmented relative atrial refractory period and illustrating an exemplary count algorithm for determining whether the time occurrences of atrial detections are repetitive enough to designate one or more time windows as blanking windows.

With reference to FIG. 11, in another exemplary count-based data processing implementation, a histogram is maintained, wherein each histogram bin corresponds to a time increment. For example, in one configuration the bins correspond to 7.8 millisecond time increments spanning between 50 milliseconds and 500 milliseconds. With respect to first histogram state 400, when processing data in an event buffer (e.g., FIG. 7B), for each P event recorded in the buffer, a P-detect count template is added to the corresponding histogram bins centered at the bin associated with the time of the P event. The P-detect count template is programmable and in the example of FIG. 11 is [1 1 3 1 1]. In the case of the first histogram state 400, three P events (P1, P2, P3) were recorded at three different times ($T_{P1}$, $T_{P2}$, $T_{P3}$). Accordingly, the histogram bins corresponding to each of times $T_{P1}$, $T_{P2}$ and $T_{P3}$ are incremented by three, while the two adjacent bins on either side of the $T_{P1}$, $T_{P2}$ and $T_{P3}$ bins are incremented by one. Upon occurrence of a subsequent ventricular event V, at histogram state 402, every bin within the corresponding ventricular-event-type histogram is decremented by one.

During the next cycle only one P event (P1) is detected at time $T_{P1}$. Accordingly, at third histogram state 404, the P-detect count template [1, 1, 3, 1, 1] is applied to time $T_{P1}$ while the histogram states at time $T_{P2}$ and $T_{P3}$ remain the same. Upon occurrence of a subsequent ventricular event V, at histogram state 406, every bin within the corresponding ventricular-event-type histogram is decremented by one. Again, during the next cycle, only one P event (P1) is detected at time $T_{P1}$. Accordingly, at fifth histogram state 408, the P-detect count template is applied to time $T_{P1}$ while the histogram state at time $T_{P2}$ and $T_{P3}$ remain the same.

Upon incrementing the histogram bins, the algorithm processes the histogram contents to determine which windows, if any, shall be "blanked", such that the corresponding P detections are ignored for purposes of atrial rate calculations. For example, the algorithm may be programmed such that only those P detections that are associated with bins having a zero count are used for atrial rate calculations, while P detections associated with bins having non-zero counts are blanked. With reference to FIG. 11, under this scenario, all bins having at least one count ("X") within the first histogram state 400, the third histogram state 404 and the fifth histogram state 408 are blanked.

In another exemplary count-based data processing implementation, two histograms are maintained. One histogram is associated with cardiac cycles initiated by intrinsic ventricular events (R waves) and the other with cycles initiated by a ventricular stimulation pulses (V paces). In this case the algorithm may be programmed such that, if the ventricular event was an R wave, the R wave histogram is processed and only those P detections that are associated with bins having a zero count are used for atrial rate calculations. P detections associated with bins having non-zero counts are blanked. Likewise, if the ventricular event was a V pace, the V pace histogram is processed and only those P detections that are associated with bins having a zero count are used for atrial rate calculations and P detections associated with bins having non-zero counts are blanked. Alternatively, both the R wave and the V pace histograms may be processed regardless of the ventricular event type, such that P detections associated with a bin is blanked if it is non-zero in either one of the histograms.

As mentioned above, the parameter determined for a time window may be derived using statistical processes other then the basic count based ones described with respect to FIGS. 9-11. For example, once such parameter may correspond to a percentage of time that an atrial detection falls within a given time window. In this case, those time windows with a percentage above a percentage threshold would be blanked. Another alternative parameter may be a running average value derived from current bin count values and next-cycle bin count values. In this case, those time windows with a running average above a running-average threshold would be blanked.

Regardless of the particular data processing implementation, the algorithm employs time based analyses to identify windows of time wherein atrial detections of ventricular events have occurred and are likely to continue to occur. While existing devices simply implement long post-ventricular atrial blanking periods to avoid non-atrial events, the algorithm described herein implements a relative atrial refractory period with one or more relatively short blanking segments inserted. As such, the algorithm effectively filters out non-atrial events, i.e., events falling within short blanked segments, from atrial rate calculations while leaving the remaining portions of the relative atrial refractory period—and the signals sense therein—available for atrial rate calculation purposes.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described.

What is claimed is:

1. A method comprising:
    during a period of time comprising a plurality of cardiac cycles, acquiring data related to the timing of ventricular events and atrial detections;
    processing the data as follows to determine if there is a time correlation between ventricular events and atrial detections:
        for each of the plurality of cardiac cycles, measuring the time between a ventricular event and each atrial detection within the cardiac cycle;
        based on the measured time, associating each atrial detection with one of a plurality of time windows;
        for each window, incrementing an atrial-detection count when an atrial detection is associated with it and decrementing the atrial-detection count when a ventricular-event count reaches a predetermined number; and
        comparing the atrial-detection count of each time window to a threshold and for each that satisfies the threshold, designating it a blanking window; and
    defining a post-ventricular atrial refractory period comprising an absolute atrial refractory period and a segmented relative atrial refractory period, wherein the segmented relative atrial refractory period includes at least one blanking window.

2. The method of claim 1 wherein a ventricular event corresponds to one of a ventricular pacing stimulus (V-paced) and an intrinsic ventricular depolarization (R-wave) and an atrial detection corresponds to one of an intrinsic atrial depolarization (P wave), a far-field R wave and a far-field T wave.

3. The method of claim 1 further comprising implementing the post-ventricular atrial refractory period during subsequent cardiac cycles.

4. The method of claim 1 further comprising monitoring the ventricular rate during the period of time and processing the data only when the ventricular rate is at or below a maximum ventricular rate.

5. The method of claim 1 wherein acquiring occurs during relative atrial refractory periods.

6. The method of claim 1 wherein processing occurs during absolute atrial refractory periods.

7. The method of claim 1 wherein the count is determined on a beat-by-beat basis.

8. The method of claim 1 wherein the count is determined periodically after a plurality of cardiac cycles.

9. The method of claim 1 wherein the ventricular event may be either a paced ventricular event (V-pace) or an intrinsic ventricular event (R-wave) and separate counts are maintained for each respective ventricular event type.

10. The method of claim 9 wherein designated blanking windows for intrinsic ventricular events are based only on counts maintained for intrinsic ventricular events.

11. The method of claim 9 wherein designated blanking windows for paced ventricular events are based only on counts maintained for paced ventricular events.

12. The method of claim 9 wherein designated blanking windows for paced ventricular events are based on counts maintained for both paced ventricular events and intrinsic ventricular events.

13. The method of claim 1 wherein the ventricular-event count corresponds to a running count of ventricular events that is reset when the predetermined number is reached.

14. A cardiac device comprising:
    a ventricular sense channel for sensing ventricular events;
    an atrial sense channel for sensing atrial detections; and a controller connected to the atrial sense channel and the ventricular sense channel and operative to:

during a period of time comprising a plurality of cardiac cycles, acquire data related to the timing of ventricular events and atrial detections;

process the data as follows to determine if there is a time correlation between ventricular events and atrial detections:

for each of the plurality of cardiac cycles, measure the time between a ventricular event and each atrial detection within the cardiac cycle;

based on the measured time, associate each atrial detection with one of a plurality of time windows;

for each window, increment an atrial-detection count when an atrial detection is associated with it and decrement the atrial-detection count when a ventricular-event count reaches a predetermined number; and compare the atrial-detection count of each time window to a threshold and for each that satisfies the threshold, designating it a blanking window; and define a post-ventricular atrial refractory period comprising an absolute atrial refractory period and a segmented relative atrial refractory period, wherein the segmented relative atrial refractory period includes at least one blanking window.

* * * * *